United States Patent [19]
Tseng et al.

[11] Patent Number: 5,956,848
[45] Date of Patent: Sep. 28, 1999

[54] SHAVING SYSTEM

[75] Inventors: Mingchih M. Tseng, Hingham; Michael J. Kwiecien, Quincy, both of Mass.

[73] Assignee: The Gillette Company, Boston, Mass.

[21] Appl. No.: 08/807,492

[22] Filed: Feb. 27, 1997

[51] Int. Cl.[6] .................................................. B26B 21/44
[52] U.S. Cl. ............................................................. 30/41
[58] Field of Search ........................... 30/41, 34.05, 77, 30/80, 81

[56] References Cited

U.S. PATENT DOCUMENTS 5,626,154  5/1997  Rogers et al. .

*Primary Examiner*—Douglas D. Watts
*Attorney, Agent, or Firm*—Fish & Richardson P.C.

[57] ABSTRACT

A shaving unit includes a composite that has a surface for engaging the user's skin. The composite includes adjacent lengthwise-extending portions, each containing a shaving aid.

50 Claims, 2 Drawing Sheets

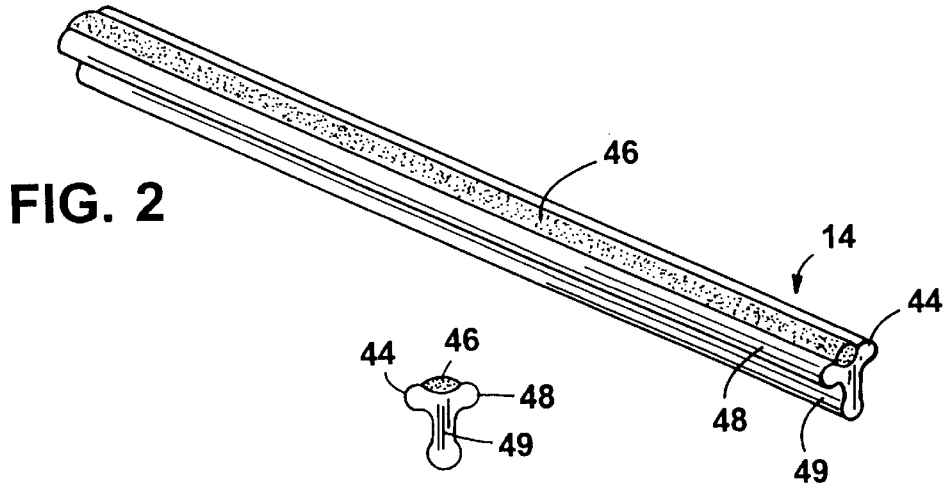
FIG. 2
FIG. 3
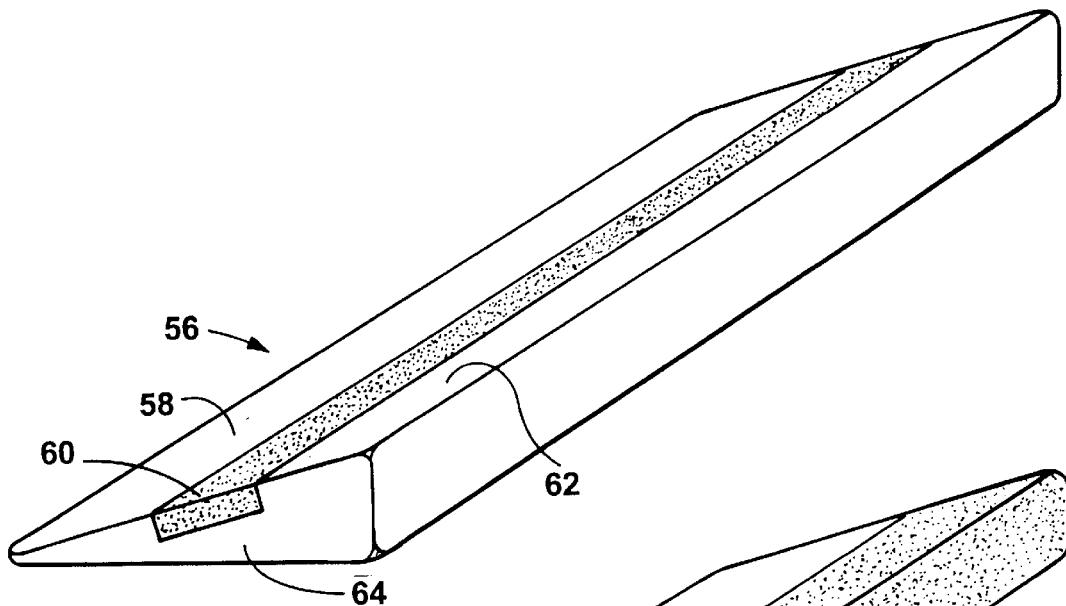
FIG. 4
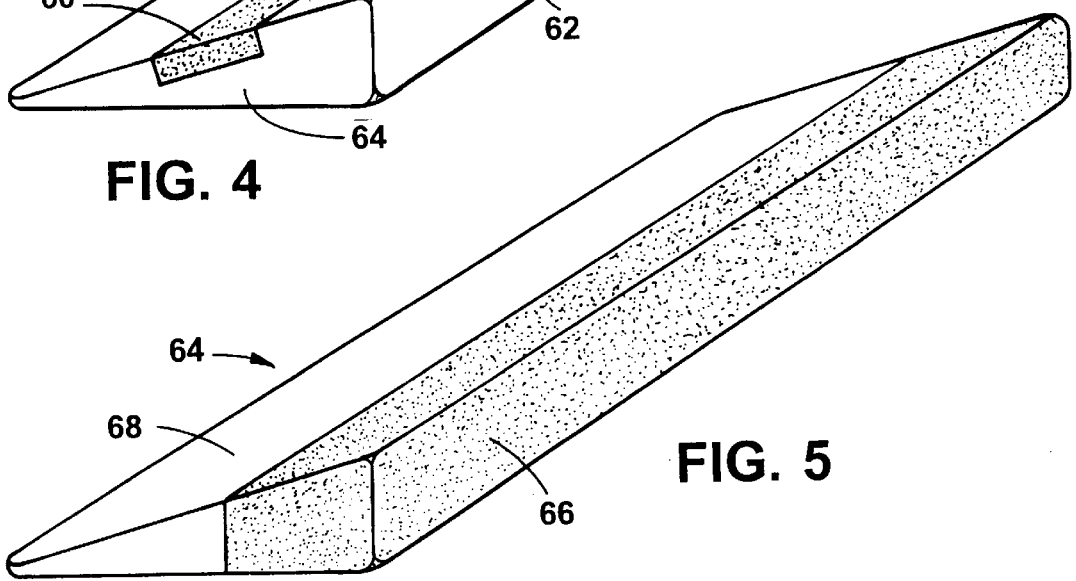
FIG. 5

SHAVING SYSTEM

This invention relates to shaving systems.

In shaving systems of the wet shave type, factors such as the frictional drag of the razor across the skin, the force needed to sever hairs, and irritation of preexisting skin damage can create a degree of shaving discomfort. Discomfort and other problems accompanying wet shaving systems can be alleviated by the application of shaving aids to the skin. Shaving aids may be applied prior to, during, or after shaving.

A number of problems accompany the use of pre- and post-applied shaving aids. Pre-applied shaving aids can evaporate or can be carried away from the site of application by repeated strokes of the razor. Post-applied shaving aids are not present on the skin during shaving and thus their application may be too late to prevent an unwanted effect. Moreover, the application of both pre-applied and post-applied shaving aids add additional steps to the shaving process.

It is known to incorporate a shaving aid into a razor by mounting a composite including the shaving aid to the razor. For example, Rogers et al., U.S. Pat. No. 5,113,585 describes a composite including a water-insoluble matrix material, a water-soluble shaving aid, and a low molecular weight release enhancing agent. When exposed to water during shaving, the water-soluble shaving aid leaches from the composition onto the skin. The release enhancing agent also dissolves in the water and improves the release of the water-soluble shaving aid from the composite.

SUMMARY OF THE INVENTION

The invention features a wet shaving system. The system includes a blade member including one or more blades and an external skin-engaging portion in proximity to the blade member. The shaving system may be, for example, a disposable shaving cartridge adapted for coupling to or uncoupling from a razor handle, or a shaving head which is integral with a razor handle so that the complete razor is discarded as a unit when the blade or blades become dulled. The blade edge cooperates with the skin engaging portion to define shaving geometry.

Significantly, the skin-engaging portion includes a polymeric shaving aid composite including two adjacent exposed lengthwise-extending portions, each containing a shaving aid. The shaving aid included in each portion may be the same or different. The composite can be, for example, an extruded composite.

A shaving aid composite having adjacent, lengthwise-extending portions provides a number of potential design advantages. For example, one portion may contain a larger quantity of water-insoluble resin than the second portion, while the second portion contains a larger quantity of shaving aid than the first portion. The first portion, then, may provide support to the second portion, which in turn may release a significant quantity of shaving aid during shaving without breaking down or causing the shaving geometry to change significantly.

Furthermore, the arrangement provides a way to incorporate incompatible shaving aids into the same shaving system. One shaving aid, for example, may chemically react with another, if they are mixed together. Likewise, a shaving aid, if included in too large a quantity in a composite that also includes another shaving aid, may unfavorably impact the wear characteristics of the composite or, for example, when the other shaving aid is a lubricous water-soluble polymer, to reduce the lubricity provided by the composite. Similarly, one shaving aid may require elevated processing temperatures during an extrusion procedure that would cause a second shaving aid to decompose. By including these shaving aids in different portions of the composite, the composite can be coextruded with different processing temperatures for each portion.

Moreover, the two portions can provide a desirable surface geometry for the composite. For example, the portions may be rounded, which may provide an enhanced skin-engaging surface on the composite. Alternatively, the exposed surface of one portion may be raised slightly relative to the second portion, which may enhance the wear characteristics of the first portion.

The invention also features a shaving system that includes two adjacent exposed lengthwise extending portions, one of which contains a colorant. The second portion has a different color than the first portion; it may, for example, contain no colorant or a colorant different from the colorant used in the first portion. The colorant in the first portion is released (e.g., by leaching or by wear) during shaving. When first used, the composite preferably has a striped appearance caused by the contrast between the two portions. One or both of the portions may also contain a shaving aid.

Other features and advantages of the invention will be apparent from the description of the preferred embodiment thereof, and from the claims.

DESCRIPTION OF THE DRAWINGS

FIG. 2 is a perspective view of a shaving aid composite in accordance with the invention.

FIG. 3 is a side view of the composite in FIG. 2.

FIG. 4 is a perspective view of a second shaving aid composite in accordance with the invention.

FIG. 5 is a perspective view of a third shaving aid composite in accordance with the invention.

DETAILED DESCRIPTION

Figure 1:
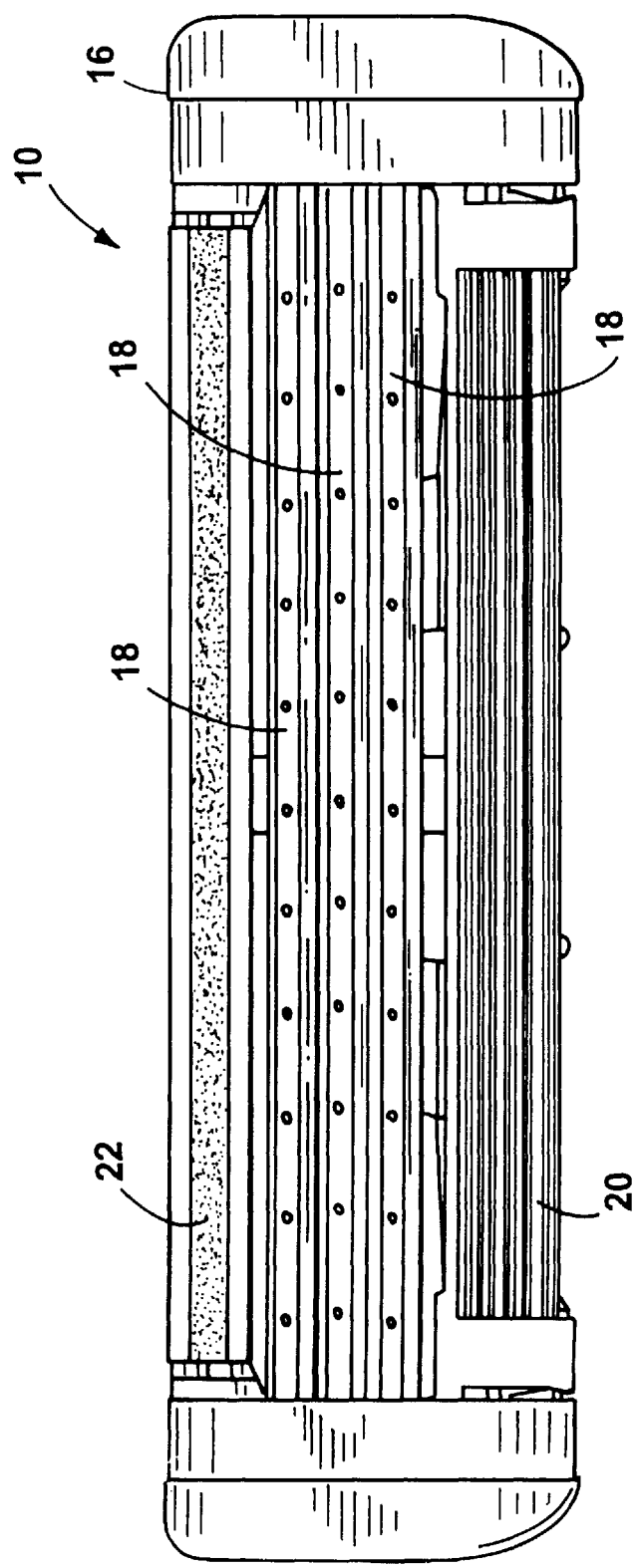
FIG. 1 is a perspective view of a razor unit in accordance with the invention.

The replaceable shaving cartridge 10 shown in FIG. 1 is of the type shown in U.S. Ser. No. 08/630,437, filed Apr. 10, 1996, which is assigned to the same assignee as the present application and is hereby incorporated by reference. It includes housing 16, which carries three blades 18, guard 20, and striped solid, polymeric shaving aid composite 22, which is in the form of an elongated insert member. The shaving aid composite is locked in an opening in the rear of the cartridge and includes a shaving aid that, during shaving is released by the composite to improve shave attributes. While shown at the rear portion of this particular shaving cartridge, the shaving aid composite may be located at any skin-engaging portion of the shaving unit and may be fabricated in any size or shape deemed appropriate. For example, the composite can be incorporated into the shaving units described in U.S. Pat. No. 4,586,225, which is incorporated by reference herein.

Referring to FIGS. 2 and 3, shaving aid composite 14 includes lengthwise-extending portions 44, 46, and 48 (each in the shape of a rounded lobe), each including a lengthwise-extending exposed surface. Composite 14 also includes connecting portion 49, which connects portions 44 and 48 and also optionally serves to lock the composite into a mating receiving portion of the cartridge. Portions 44 and 48 and connecting portion 49 have the same compositions and, together, surround all but the exposed face of portion 46. They can provide support for portion 46. Portions 44, 46, and 48 each may be, for example, between 1.20 inches and 1.35 inches (more preferably between 1.25 inches and 1.275 inches) in length, and between about 0.02 inch to 0.04 inch in width, such that the composite is between 0.07 inch and 0.11 inch (more preferably between 0.085 inch and 0.095 inch) in width.

Portions 44, 46, and 48 each contains a water insoluble polymer, optionally in different amounts, and a shaving aid. They may contain the same shaving aid, or different shaving aids. In one embodiment portions 44 and 48 are identical, and contain the same shaving aid, while portion 46 contains a different shaving aid, optionally in combination with the same shaving aid contained in portions 44 and 48.

Each portion also may contain other conventional shaving and composite ingredients, such as low molecular weight water-soluble release enhancing agents such as polyethylene glycol (e.g., 1–10% by weight), water-swellable release enhancing agents such as cross-linked polyacrylics (e.g., 2–7% by weight), colorants, antioxidants and preservatives. Water-soluble release enhancing agents are described in U.S. Pat. No. 5,113,585, which is hereby incorporated by reference. Water-swellable release-enhancing agents are described in U.S. Ser. No. 08/121,153, filed Sep. 13, 1993, which is assigned to the same assignee as the parent application and is hereby incorporated by reference. Portions that contain a colorant can be designed to release the colorant, and change color, during shaving, preferably in response to wear of the portion. A portion may contain, for example, between about 0.1% and about 5.0% (preferably between about 0.5% and 3%) colorant by weight.

Suitable water-insoluble polymers which can be used include polyethylene, polypropylene, polystyrene, butadiene-styrene copolymer (e.g. medium and high impact polystyrene), polyacetal, acrylonitrile-butadiene-styrene copolymer, ethylene vinyl acetate copolymer and blends such as polypropylene/polystyrene blend.

Preferably, each portion includes about 5% to 50%, more preferably about 15 to 40%, and most preferably about 20 to 35% by weight of the water-insoluble polymer. The more preferred water-insoluble polymer is polystyrene, preferably a general purpose polystyrene such as BASF 2824 or a high impact polystyrene (i.e. polystyrene-butadiene), such as Mobil 4324. The portion should contain a sufficient quantity of water-insoluble polymer to provide adequate mechanical strength, both during production and use.

A shaving aid is a substance that enhances shaving performance. It may, for example, improve shaving comfort (e.g., by lubricating the skin, improve shaving efficiency, condition the beard, or condition the skin. Examples of shaving aids include lubricous water-soluble polymer such as polyethylene oxide, polyvinyl pyrrolidone, polyacrylamide, hydroxypropyl cellulose, polyvinyl imidazoline, and polyhydroxyethylmethacrylate; beard hair softeners; oils such as silicone oil and mineral oil; substances that enhance the healing or stop the bleeding of the skin; essential oils such as menthol, eugenol, eucalyptol, safrol, and methyl salicylate; rinsing aids; non-volatile cooling agents; inclusion complexes of skin-soothing agents with cyclodextrin; fragrances; vitamin E (including common forms of vitamin E such as vitamin E acetate); vitamin A and B-carotene; panthenol and aloe; antipruritic/counterirritant materials; antimicrobial/keratolytic materials; anti-inflammatory agents; and astringents.

Enough shaving aid should be included to provide the desired benefit. A portion may contain, for example, about 20% to about 80%, more preferably about 40% to about 75%, by weight of a lubricous water soluble polymer. A portion also may include, for example, about 0.01% to about 5.0%, more preferably about 0.05 to about 1.0%, vitamin E (or common forms of vitamin E) by weight.

The preferred lubricous water-soluble polymer is polyethylene oxide. The more preferred polyethylene oxides generally are known as POLYOX (available from Union Carbide Corporation) or ALKOX (available from Meisei Chemical Works, Kyoto, Japan). These polyethylene oxides will preferably have molecular weights of about 100,000 to 6 million, most preferably about 300,000 to 5 million. The most preferred polyethylene oxide comprises a blend of about 40 to 80% of polyethylene oxide having an average molecular weight of about 5 million (e.g. POLYOX COAGULANT) and about 60 to 20% of polyethylene oxide having an average molecular weight of about 300,000 (e.g. POLYOX WSR-N-750). The polyethylene oxide blend may also advantageously contain up to about 10% by weight of a low molecular weight (i.e., MW<10,000) polyethylene glycol such as PEG-100.

The shaving aid composite may be fabricated by any appropriate method, including injection molding and extrusion, the latter being preferred.

A preferred shaving aid composite is provided below. Portions 44 and 48 (and connecting portion 49) are the same in each example. One shaving aid composite includes a central blue portion (46), the other a central green portion (46). The colorant in the central portion is released during shaving, generally by the gradual wearing away of that portion during use, thereby indicating through color change that the shaving aid originally contained in the central portion is no longer being delivered.

Because of the rounded lobe geometry of portions 44, 46, and 48, including the significant recesses at the junctions of portions 44 and 46 and portions 46 and 48, the shaving aid composite may have more surface area available to contact the skin than, for example, a shaving aid composite having a flat skin-engaging surface. This may provide increased lubrication for the skin and may reduce the time it takes for portion 46 to wear away. The raised elevation of the exposed surface of portion 46 relative to the exposed surface of portions 44 and 48 also may enhance the rate of wear of portion 46.

In the chart, the components used in the shaving aid composites are provided in the first column on the left. The quantities of each component in portions 44 and 48 and connecting portion 49 are provided in the second column. The third and fourth columns provide ranges for the quantities of components that are used in the shaving aid composite including a central blue portion (46). The fifth and sixth columns provide ranges for the quantities of components that are used in the shaving aid composite including a central green portion (46).

| Component Description | Portions 44, 48, and 49 | Portion 46 (Blue) | | Portion 46 (Green) | |
| --- | --- | --- | --- | --- | --- |
| | | HI | LO | HI | LO |
| BASF 2824 (CPS) | 33.54% | 22.50% | 32.50% | 23.00% | 33.00% |
| Polyox Coag. | 33.02% | 32.86% | 38.86% | 32.86% | 38.86% |
| Polyox WSR N750 | 21.99% | 0.00% | 21.99% | 0.00% | 21.99% |
| N-750 w/Vit E[2] | | 0.00% | 21.99% | 0.00% | 21.99% |
| Dow 4500 PEG | 10.00% | 10.00% | 10.00% | 10.00% | 10.00% |
| Coz Stripwte.[3] | 1.20% | 0.00% | 0.00% | 0.00% | 0.00% |

-continued

| Component Description | Portions 44, 48, and 49 | Portion 46 (Blue) HI | Portion 46 (Blue) LO | Portion 46 (Green) HI | Portion 46 (Green) LO |
|---|---|---|---|---|---|
| B215 Irganox[4] | 0.25% | 0.25% | 0.25% | 0.25% | 0.25% |
| t-green[5] | | 0.00% | 0.00% | 3.50% | 3.50% |
| Blue 1811-C[6] | | 1.00% | 1.00% | 0.00% | 0.00% |
| | 100.00% | | | | |

[1]High impact polystyrene (e.g., Mobil 4324) could also be used.
[2]Vitamin E liquid (from Hoffman-LaRoche) spray coated on powdered N750 (4% load).
[3]Polystyrene-based color concentrate containing TiO$_2$ (white) (from Coz Corp.).
[4]Antioxidant (from Ciba Geigy).
[5]Polystyrene-based color concentrate (T-Green) (from Coz Corp.).
[6]Polystyrene-based color concentrate (GN-Blue) (from Coz Corp.).

A preferred shaving aid composite has the following composition:

| Portions 44, 48, and 49 | |
|---|---|
| Component | Weight % |
| Mobil 4324 | 33.54% |
| Polyox Coag. | 33.02% |
| Polyox WSR N750 | 21.99% |
| Dow 4500 PEG | 10.00% |
| Coz Stripwte. | 1.20% |
| B215 Irganox | 0.25% |
| TOTAL | 100.00% |

| Portion 46 | |
|---|---|
| Component | Weight % |
| BASF 2824 CPS | 24.00% |
| Polyox Coag. | 38.86% |
| Polyox WSR N750 | 3.90% |
| Dow 4500 PEG | 10.00% |
| GN Blue | 1.00% |
| B215 Irganox | 0.25% |
| Polyox WSR N-750 | 21.99% |
| w/Vit E (4%) | |
| TOTAL | 100.00% |

The shaving aid composites can be prepared by conventional coextrusion or molding methods known to those skilled in the art. For example, the components of the composite may be supplied by two separate melting/pumping (plastics extruders), each consisting of a heated barrel, a pumping screw, a motor drive for that screw and a control system for the entire system. The materials of the composite are fed in powder form into their respective extruders (e.g., single screw type manufactured by Davis Standard). The extruders can operate at the same or different speeds and the same or different temperatures. The barrel temperature for each extruder can be ramped in three zones from 325° F. to 375° F.; a fourth heater at the die/barrel connection can also be set to 375° F., and a fifth heater at the die can range from 375° F. to 400° F. Via rugged weldments the molten streams of the components are brought together to form the composite. Portion 46 can be precisely located on a portion (combination 44, 48, and 49) through accurately machined pathways in the die head. Because they have different compositions, the two molten materials are brought together at the last possible moment before exiting the die. Both materials exit the die head in a size and shape approximating that of the final product. The final dimensions are achieved using a series of forming rollers as the extrudate is cooled. The composite is typically extruded at a rate of 50 feet per minute.

The combined molten materials are drawn from the die head into the sizing/cooling device at a constant speed such that its cross section is always constant. Under a bath of cool dry air the molten material is cooled until no longer pliable. Once cooled, the composite can be cut to the appropriate length and attached to a razor cartridge.

Other examples of shaving aid composites may include the same composition for portions 44, 48, and connecting portion 49, and a central portion (46) that contains about 90% of the composition used for portions 44 and 48, plus the following:

Example A—1% blue pigment and 10% Aloe.
Example B—1% blue pigment and 10% Menthol.
Example C—10% Frescolat (a menthol analog).
Example D—10% Mineral Oil/Vit. E.
Example E—10% Silicone fluid 1401.
Example F—5% Vit. E and 5% Panthenol.
Example G—10% Triclosan DP300 (an antimicrobial).

In other examples, portions 44 and 48 have the composition described above. The central portion contained the following percentages of the composition used in portions 44 and 48 (% Comp.), plus additional ingredients, as follows:

Example H—95% Comp. and 5% Triclosan DP300.
Example I—93% Comp. and 6% Menthol and 1% Silicone copolymer.
Example J—94% Comp. and 6% Menthol.
Example K—85% Comp. and 10% polyethylene oxide (60:40 Polyox blend previously used in portion 44) and 5% Salsorb.

In another example, central portion 46may be composed of 80% Polyox (60:40 Polyox blend previously used in portion 44) and 20% nylon 12.

In another example, central portion 46 may contain the following ingredients:

Example L—80% Polyox (60:40 Polyox blend previously used in portion 44) and 14% polystyrene and 3% PEG 100 and 3% PVA.
Example M—70% amorphous nylon (Zytel 330) and 30% Polyox (60/40).
Example N—77.75% Polyox (60:40 Polyox blend previously used in portion 44) and 10% PEG 100 and 0.25% Irganox and 2% green pigment and 10% Vit. E.

Other embodiments are within the claims. For example, referring to FIG. 4, a wedge-shaped shaving aid composite 56 includes lengthwise-extending portions 58, 60, and 62, each including a lengthwise-extending exposed surface. Shaving aid composite 56 also includes connection portion 64. Portions 58, 60, 62, and 64 can have, for example, the same compositions as portions 44, 46, 48, and 49, respectively, and may be made by conventional co-extrusion or molding techniques. Shaving aid composite 56 can be attached to a shaving cartridge, e.g., the shaving cartridge used in Atra®, by gluing the composite to the recess in the cartridge.

Alternatively, referring to FIG. 5, the wedge-shaped shaving composite 64 may include two lengthwise-extending portions 66 and 68. Portion 66 can contain 90% Comp., 1% blue pigment, and 10% Menthol or Aloe. Portion 68 can contain 100% Comp. with a small quantity of white pigment. The shaving aid composite shown in FIGS. 2 and 3 also may include only two lengthwise-extending portions.

We claim:

1. A wet shaving system comprising a blade member and a skin-engaging portion in proximity to said blade member, said skin-engaging portion comprising a solid polymeric shaving aid composite including a first exposed, lengthwise-extending portion containing a first shaving aid, and an adjacent, second exposed lengthwise-extending portion containing a second shaving aid, wherein said first exposed lengthwise-extending portion has a different composition than said second exposed lengthwise-extending portion.

2. The shaving system of claim 1, wherein said first shaving aid and said second shaving aid are the same.

3. The shaving system of claim 1, wherein said first shaving aid is different from said second shaving aid.

4. The shaving system of claim 3, wherein said first shaving aid is incompatible with said second shaving aid.

5. The shaving system of claim 1, wherein said first shaving aid would adversely affect the structural integrity of said second portion if said second portion contained the quantity of said first shaving aid contained in said first portion.

6. The shaving system of claim 1, wherein said first portion further comprises a first water-insoluble polymer and said second portion further comprises a second water-insoluble polymer.

7. The shaving system of claim 6, wherein said first water-insoluble polymer and said second water-insoluble polymer independently are selected from the group consisting of polyethylene, polypropylene, polystyrene, butadiene-styrene copolymer, polyacetal, acrylonitrile-butadiene-styrene copolymer, and ethylene vinyl acetate copolymer.

8. The shaving system of claim 1, wherein said first portion further contains a colorant.

9. The shaving system of claim 1, wherein said first shaving aid comprises a lubricous water-soluble polymer.

10. The shaving system of claim 9, wherein said water-soluble polymer comprises polyethylene oxide.

11. The shaving system of claim 1 or 10, wherein said first portion further comprises a water-insoluble polymer.

12. The shaving system of claim 1, wherein said first shaving aid and said second shaving aid independently are selected from the group consisting of polyethylene oxide, polyvinyl pyrrolidone, polyacrylamide, hydroxypropyl cellulose, polyvinyl imidazoline, and polyhydroxyethyl-methacrylate; beard hair softeners; oils such as silicone oil and mineral oil; substances that enhance the healing or stop the bleeding of the skin; essential oils such as menthol, eugenol, eucalyptol, safrol, and methyl salicylate; rinsing aids; non-volatile cooling agents; inclusion complexes of skin-soothing agents with cyclodextrin; fragrances; vitamin E; vitamin A and B-carotene; panthenol and aloe; antipruritic/counterirritant materials; antimicrobial/keratolytic materials; anti-inflammatory agents; and astringents.

13. The shaving system of claim 1, wherein said second shaving aid comprises polyethylene oxide and said first shaving aid comprises vitamin E.

14. The shaving system of claim 1, wherein said second shaving aid comprises polyethylene oxide and said first shaving aid comprises aloe.

15. The shaving system of claim 13 or 14 wherein said first shaving aid further comprises polyethylene oxide.

16. The shaving system of claim 1, wherein said shaving aid composite further comprises a third, exposed lengthwise-extending portion, containing a third shaving aid, adjacent said first portion, such that said first portion is located between said second and third portions.

17. The shaving system of claim 16, wherein said second shaving aid and said third shaving aid comprises polyethylene oxide and said first shaving aid comprises vitamin E.

18. The shaving system of claim 16, wherein said second shaving aid and said third shaving aid comprises polyethylene oxide and said first shaving aid comprises aloe.

19. The shaving system of claim 17 or 18, wherein said first shaving aid further comprises polyethylene oxide.

20. The shaving system of claim 19, wherein said first portion, said second portion, and said third portion each further comprises a water-insoluble polymer.

21. The shaving system of claim 20, wherein said first portion comprises about 10% to about 40% by weight of said water-insoluble polymer, about 20% to about 80% of said polyethylene oxide, and about 0.5% to about 2% of said vitamin E and/or aloe, and wherein said second portion and said third portion each comprises about 15% to about 40% of said water-insoluble polymer and about 20% to about 80% of said polyethylene oxide.

22. The shaving system of claim 21, wherein said water-insoluble polymer is selected from the group consisting of polyethylene, polypropylene, polystyrene, butadienestyrene copolymer, polyacetal, acrylonitrile-butadiene-styrene copolymer, and ethylene vinyl acetate copolymer.

23. The shaving system of claim 16, wherein said second portion and said third portion provide support for said first portion.

24. The shaving system of claim 16, wherein said first portion further includes a colorant that is released during shaving.

25. The shaving system of claim 16, wherein said second portion and said third portion further comprise a colorant that is released during shaving.

26. The shaving system of claim 16, wherein said shaving aid composite includes a connecting portion that extends under said first portion and connects said second portion and said third portion.

27. The shaving system of claim 26, wherein said connecting portion, said second portion, and said third portion have the same composition.

28. The shaving system of claim 1, wherein said first portion and said second portion have the same length.

29. The shaving system of claim 1, wherein said first portion and said second portion each has a length of about 1.20 inches to 1.35 inches.

30. The shaving system of claim 1, wherein said first portion and said second portion each has a width of about 0.02 inch to 0.04 inch.

31. The shaving system of claim 1, wherein said shaving composite is an extruded composite.

32. The shaving system of claim 16 wherein said third portion and said second portion have the same composition.

33. The shaving system of claim 16 wherein said third shaving aid and said second shaving aid are the same.

34. The shaving system of claim 16 wherein said first portion contains a larger quantity of shaving aid than said second and third portions.

35. The shaving system of claim 34 wherein said first, second and third shaving aids each comprise polyethylene oxide.

36. The shaving system of claim 16 wherein said first shaving aid is different from said second and third shaving aids.

37. The shaving system of claim 36 wherein said first portion includes, in addition to said first shaving aid, a further shaving aid which is the same as said second and third shaving aids.

38. The shaving system of claim 37 wherein said further shaving aid and said second and third shaving aids each comprise polyethylene oxide.

39. The shaving system of claim 35 or 38, wherein said shaving aid composite includes a connecting portion that extends under said first portion and connects said second portion and said third portion.

40. The shaving system of claim 39, wherein said first portion, said second portion, said third portion and said connecting portion, each comprises a water insoluble polymer.

41. The shaving system of claim 40, wherein said connecting portion, said second portion, and said third portion have the same composition.

42. The shaving system of claim 39, wherein said first portion further includes a colorant that is released during shaving by gradual wearing away of said first portion during use, thereby indicating that said first shaving aid is depleted.

43. The shaving system of claim 41, wherein said first portion further includes a colorant that is released during shaving by gradual wearing away of said first portion during use, thereby indicating that said first shaving aid is depleted.

44. The shaving system of claim 6, wherein said first shaving aid is different from said second shaving aid.

45. The shaving system of claim 44, wherein said first portion includes, in addition to said first shaving aid, a further shaving aid which is the same as said second shaving aid.

46. The shaving system of claim 45, wherein said further shaving aid and said second shaving aid each comprise polyethylene oxide.

47. The shaving system of claim 6, wherein said first shaving aid and said second shaving aid each comprise polyethylene oxide.

48. The shaving system of claim 6, wherein said first water-insoluble polymer and said second water-insoluble polymer independently are selected from the group consisting of polystyrene and butadiene-styrene copolymer.

49. The shaving system of claim 40, wherein said water-insoluble polymer is selected from the group consisting of polystyrene and butadiene-styrene copolymer.

50. The shaving system of claim 1 or 16, wherein said shaving system comprises three blade members.

* * * * *

UNITED STATES PATENT AND TRADEMARK OFFICE
CERTIFICATE OF CORRECTION

PATENT NO. : 5,956,848 Page 1 of 3
DATED : September 28, 1999
INVENTOR(S) : Dr. Michael Kwiecien and Mingchih M. Tseng It is certified that error appears in the above-identified patent and that said Letters Patent is hereby corrected as shown below:

<u>Title page,</u>
Item [56], References Cited, U.S. PATENT DOCUMENTS, please insert the following:

| | | |
|---|---|---|
| -- 5,454,164 | 10/95 | Yin et al. |
| 5,430,939 | 7/95 | Johnston |
| 5,416,973 | 5/95 | Brown et al. |
| 5,410,810 | 5/95 | Gillibrand |
| 5,388,331 | 2/98 | Doroodian-Shoja Siamak |
| 5,349,750 | 9/94 | Tseng |
| 5,347,716 | 9/94 | Crook |
| 5,345,680 | 9/94 | Vreeland et al. |
| 5,340,581 | 8/94 | Tseng et al. |
| 5,249,361 | 10/93 | Apprille, Jr. et al. |
| 5,240,107 | 8/93 | Casale |
| 5,228,478 | 7/93 | Kleisle |
| 5,191,712 | 3/93 | Crook et al. |
| 5,161,307 | 11/92 | Althaus |
| 5,134,775 | 8/92 | Althaus et al. |
| 5,119,557 | 6/92 | Kaiko |
| 5,113,585 | 5/92 | Rogers et al. |
| 5,095,620 | 3/92 | Althaus |
| 5,095,619 | 3/92 | Davis et al. |
| 5,079,839 | 1/92 | Conrad, Jr. et al. |
| 5,063,667 | 11/91 | Jacobson |
| 5,062,209 | 10/91 | Rais |
| 5,056,222 | 10/91 | Miller et al. |
| 5,056,221 | 4/91 | Theone |
| 5,005,287 | 4/91 | Ritter |
| 4,875,287 | 10/89 | Creary et al. |
| 4,872,263 | 10/89 | Etheredge, III |
| 4,850,106 | 7/89 | Braun et al. |
| 4,802,255 | 2/89 | Breuer et al. |
| 4,778,640 | 10/88 | Braun et al. |
| 4,777,722 | 10/88 | Trotta |
| 4,697,342 | 10/87 | Ferraro |
| 4,692,986 | 9/87 | Motta et al. |
| 4,683,096 | 7/87 | Ferrarp |

UNITED STATES PATENT AND TRADEMARK OFFICE
CERTIFICATE OF CORRECTION

PATENT NO.   : 5,956,848
DATED        : September 28, 1999
INVENTOR(S)  : Dr. Michael Kwiecien and Mingchih M. Tseng It is certified that error appears in the above-identified patent and that said Letters Patent is hereby corrected as shown below:

Item [56], U.S. PATENT DOCUMENTS, cont'd.

| | | |
|---|---|---|
| 4,624,051 | 11/86 | Apprille, Jr. et al. |
| 4,604,604 | 8/86 | Mann |
| 4,586,255 | 5/86 | Jacobson |
| 4,381,293 | 4/83 | Michel |
| 4,268,958 | 5/81 | Hilbert |
| 4,208,984 | 6/80 | Glanzman |
| 4,201,599 | 5/80 | Morgans |
| 4,170,821 | 10/79 | Booth |
| 3,879,844 | 4/75 | Griffiths |
| 3,618,563 | 11/71 | Singer |
| 3,512,256 | 5/70 | Snyder |
| 3,394,456 | 7/68 | Gatz |
| 3,229,659 | 1/66 | Sciascia |
| 2,885,993 | 5/59 | Murphy |
| 2,812,575 | 11/57 | Abbott et al. |
| 2,750,664 | 6/56 | Merlo |
| 2,703,451 | 3/55 | Hensel et al. |
| 2,680,290 | 6/54 | Steinberg |
| 2,326,774 | 8/43 | Freedman |

FOREIGN PATENT DOCUMENTS

| | | |
|---|---|---|
| WO 96/13360 | 9/96 | PCT |
| WO 96/01172 | 1/96 | PCT |
| WO 96/04112 | 2/96 | PCT |
| WO 95/22444 | 8/95 | PCT |
| WO 95/20472 | 8/95 | PCT |
| 7-124,344 | 5/95 | Japan |
| WO 94/04325 | 3/94 | PCT |
| WO 93/16135 | 8/93 | PCT |
| WO 93/15883 | 8/93 | PCT |
| 0 550 835 Al | 12/92 | EPC |
| WO 92/15278 | 9/92 | PCT |
| EP 0 313 184 B1 | 6/92 | EPC |
| EP 0 287 387 B1 | 9/91 | EPC |
| FR 2 637 528 Al | 4/90 | France |

UNITED STATES PATENT AND TRADEMARK OFFICE
CERTIFICATE OF CORRECTION

PATENT NO.    : 5,956,848
DATED         : September 28, 1999
INVENTOR(S)   : Dr. Michael Kwiecien and Mingchih M. Tseng It is certified that error appears in the above-identified patent and that said Letters Patent is hereby corrected as shown below:

Item [56], FOREIGN PATENT DOCUMENTS, cont'd.,

EP 0 348 627 Al    1/90    EPC
        GB 2 024 082 A    1/90    UK
        DE 36 04 983 A1    8/87    Germany
        GB 2 183 523 A    6/87    UK
        DE 35 33 238 A1    3/87    Germany
        FR 2 563 142 Al    10/85    France
        133093    4/33    Austria --

<u>Column 8,</u>
Line 24, delete "butadienestyrene" and insert -- butadiene-styrene --.

Signed and Sealed this

Fifteenth Day of April, 2003

JAMES E. ROGAN
*Director of the United States Patent and Trademark Office*